US011110036B2

(12) United States Patent
Bauer et al.

(10) Patent No.: US 11,110,036 B2
(45) Date of Patent: Sep. 7, 2021

(54) FEEDING SET AND ENTERAL FEEDING PUMP ASSEMBLY

(71) Applicant: Medline Industries, Inc., Northfield, IL (US)

(72) Inventors: Lisa Bauer, Buffalo Grove, IL (US); Douglas Komandt, Chicago, IL (US); Morgan Uridil, Evanston, IL (US); Luke Stevens, Long Grove, IL (US); Michael Turturro, Arlington Heights, IL (US); Paulina Lowkis, Barrington, IL (US)

(73) Assignee: Medline Industries, Inc., Northfield, IL (US)

( * ) Notice: Subject to any disclaimer, the term of this patent is extended or adjusted under 35 U.S.C. 154(b) by 127 days.

(21) Appl. No.: 16/458,900

(22) Filed: Jul. 1, 2019

(65) Prior Publication Data

US 2021/0000694 A1 Jan. 7, 2021

(51) Int. Cl.
*A61J 15/00* (2006.01)
*A61M 5/142* (2006.01)
(Continued)

(52) U.S. Cl.
CPC ...... *A61J 15/0092* (2013.01); *A61M 5/14232* (2013.01); *A61M 5/16813* (2013.01);
(Continued)

(58) Field of Classification Search
CPC ............ B67D 1/108; A61M 2039/224; A61M 2039/2486; A61M 2039/2473; A61M 2005/244; A61M 5/1414
See application file for complete search history.

(56) References Cited

U.S. PATENT DOCUMENTS

| 1,607,053 A | 11/1926 | Eshton |
| 2,756,740 A | 7/1956 | Deane |

(Continued)

FOREIGN PATENT DOCUMENTS

| EP | 2434635 | 3/2012 |
| EP | 3325044 | 5/2018 |

(Continued)

OTHER PUBLICATIONS

PCT Search Report and Written Opinion from corresponding International Application No. PCT/US2020/036099 dated Sep. 18, 2020; 13 pages.

(Continued)

*Primary Examiner* — Bhisma Mehta
*Assistant Examiner* — Robert F Allen
(74) *Attorney, Agent, or Firm* — Fitch, Even, Tabin & Flannery LLP

(57) ABSTRACT

In some embodiments, apparatuses and methods are provided herein useful to provide fluid nutrition and hydration. In one illustrative example, a feeding set for use with a peristaltic enteral feeding pump has sections of flexible tubing or conduit, a dispensing control valve that is in fluid communication with the tubing, and a retention disk. In some configurations, the feeding set has as attachment mechanism, which may be formed by one clips or hooks extending from the dispensing control valve and coupling geometry of the retention disk. By some approaches, the clips or hooks and the coupling geometry are configured to attach the feeding set with the pump, such as by attaching the feeding set to an internal panel of the feeding pump. In operation, the feeding set and pump are used to move fluid nutrition and hydration from a container or bag to the patient in a controlled manner.

25 Claims, 19 Drawing Sheets

(51) Int. Cl.
*A61M 5/168* (2006.01)
*A61M 39/28* (2006.01)

(52) U.S. Cl.
CPC ......... *A61M 39/28* (2013.01); *A61M 5/16877* (2013.01); *A61M 2202/0482* (2013.01)

(56) References Cited

U.S. PATENT DOCUMENTS

| | | |
|---|---|---|
| 2,760,262 A | 8/1956 | Homan |
| 2,982,434 A | 5/1961 | Hidding |
| 3,195,759 A | 7/1965 | Beacham |
| 3,220,591 A | 11/1965 | Hidding |
| 3,556,453 A | 1/1971 | Hall |
| 3,630,477 A | 12/1971 | Stadler |
| 3,638,823 A | 2/1972 | McCoy |
| 3,807,679 A | 4/1974 | Burke |
| 4,045,070 A | 8/1977 | Geisinger |
| 4,634,089 A | 1/1987 | Wright |
| 4,930,532 A | 6/1990 | Mayer |
| 5,135,125 A | 8/1992 | Andel |
| 5,174,534 A | 12/1992 | Mitchell |
| D333,184 S | 2/1993 | Taylor |
| D334,620 S | 4/1993 | Taylor |
| D348,384 S | 7/1994 | Karsten |
| D354,350 S | 1/1995 | Pryor |
| 5,470,037 A | 11/1995 | Willis |
| 5,490,658 A | 2/1996 | Coward |
| 5,514,102 A | 5/1996 | Winterer |
| 5,549,074 A | 8/1996 | Hui |
| D376,974 S | 12/1996 | Chen |
| 5,647,520 A | 7/1997 | McDaid |
| 5,720,721 A | 2/1998 | Dumas |
| 5,807,333 A | 9/1998 | Osborne |
| 5,816,553 A | 10/1998 | Brown |
| D404,128 S | 1/1999 | Huebner |
| 5,934,222 A | 8/1999 | Hwang |
| 5,944,697 A | 8/1999 | Biche |
| D418,916 S | 1/2000 | Bastable |
| 6,129,703 A | 10/2000 | Beneke |
| D438,618 S | 3/2001 | Solem |
| 6,224,578 B1 | 5/2001 | Davis |
| 6,280,415 B1 | 8/2001 | Johnson |
| 6,280,422 B1 | 8/2001 | Sanchez-Browning |
| D450,233 S | 11/2001 | Ward |
| D450,512 S | 11/2001 | Gottwald |
| D451,326 S | 12/2001 | Gottwald |
| 6,435,134 B1 | 8/2002 | Ho |
| 6,561,129 B1 | 5/2003 | Cheng |
| D475,878 S | 6/2003 | Knable, III |
| D492,871 S | 7/2004 | Alves |
| D497,993 S | 11/2004 | Dixon |
| D502,773 S | 3/2005 | Abry |
| D506,668 S | 6/2005 | Black |
| D513,419 S | 1/2006 | Morrison |
| 7,092,797 B2 | 8/2006 | Gaines |
| 7,447,566 B2 | 11/2008 | Knauper |
| D583,053 S | 12/2008 | Zhukauskas |
| 7,726,174 B2 | 6/2010 | Riley |
| 7,763,005 B2 | 7/2010 | Knauper |
| 7,818,992 B2 | 10/2010 | Riley |
| 8,021,322 B1 | 9/2011 | Francis |
| D649,641 S | 11/2011 | Guttulsrud |
| 8,142,404 B2 | 3/2012 | Knauper |
| 8,177,736 B2 | 5/2012 | Kopperschmidt |
| D663,417 S | 7/2012 | Meyer |
| 8,225,639 B2 | 7/2012 | Riley |
| D669,586 S | 10/2012 | Meyer |
| D672,037 S | 12/2012 | Miller |
| 8,574,190 B2 | 11/2013 | Francis |
| D707,355 S | 6/2014 | Bow |
| 9,101,712 B2 | 8/2015 | Denis |
| 9,402,789 B2 | 8/2016 | Knauper |
| 9,408,968 B2 | 8/2016 | Browne |
| 9,424,020 B2 | 8/2016 | Borges |
| D783,814 S | 4/2017 | Hanuka |
| D789,540 S | 6/2017 | Gyorgy |
| 9,710,610 B2 | 7/2017 | Flynn |
| D796,667 S | 9/2017 | Manandhar |
| D799,056 S | 10/2017 | Bourgeois |
| 9,820,916 B2 | 11/2017 | Boulanger |
| 9,852,263 B2 | 12/2017 | Harr |
| 9,871,866 B2 | 1/2018 | Borges |
| D812,456 S | 3/2018 | Nolta |
| 9,909,688 B2 | 3/2018 | Gaines |
| 9,974,902 B2 | 5/2018 | Holderle |
| 10,215,305 B2 | 2/2019 | Gaines |
| 10,219,985 B2 | 3/2019 | Hudson |
| 10,227,971 B2 | 3/2019 | Hudson |
| 10,293,103 B2 | 5/2019 | Adams |
| 10,387,624 B2 | 8/2019 | Jedwab |
| D861,863 S | 10/2019 | Leonard |
| 10,426,709 B2 | 10/2019 | Harr |
| D866,748 S | 11/2019 | Khabiri |
| 2003/0062049 A1 | 4/2003 | Kolobow |
| 2003/0212381 A1 | 11/2003 | Whitehead, III |
| 2005/0165304 A1 | 7/2005 | Albertelli |
| 2006/0173412 A1* | 8/2006 | Susi ............ F04B 43/082 604/123 |
| 2008/0119822 A1 | 5/2008 | Knauper |
| 2009/0139530 A1 | 6/2009 | Landis |
| 2010/0057017 A1 | 3/2010 | Pappas |
| 2012/0123322 A1* | 5/2012 | Scarpaci ............ G01V 8/20 604/29 |
| 2013/0161470 A1 | 6/2013 | Alvares |
| 2014/0031784 A1* | 1/2014 | Flynn ............ A61M 5/142 604/500 |
| 2016/0058673 A1 | 3/2016 | Francis |
| 2016/0235630 A1 | 8/2016 | Zuijderduin |
| 2016/0361492 A1 | 12/2016 | Nunez |
| 2017/0105903 A1* | 4/2017 | Gallotto ............ A61M 5/14 |
| 2017/0173257 A1 | 6/2017 | Sarna |
| 2017/0197026 A1 | 7/2017 | Kesselman |
| 2018/0207360 A1 | 7/2018 | Juretich |
| 2018/0234499 A1 | 8/2018 | Borges |
| 2018/0236168 A1 | 8/2018 | Holderle |
| 2018/0325373 A1 | 11/2018 | Rodger |
| 2019/0142699 A1 | 5/2019 | Hudson |
| 2019/0216688 A1 | 7/2019 | Ganter |
| 2019/0240397 A1 | 8/2019 | Adams |
| 2019/0247643 A1 | 8/2019 | Merchant |
| 2019/0358387 A1 | 11/2019 | Elbadry |

FOREIGN PATENT DOCUMENTS

| | | |
|---|---|---|
| WO | 2008059495 | 5/2008 |
| WO | 2016152238 | 9/2016 |
| WO | 2018177765 | 10/2018 |
| WO | 2019148900 | 8/2019 |

OTHER PUBLICATIONS

Medline Industries, Inc., Pictures of Medline EntraFlo Nutrition Delivery System, publicly available Nov. 1, 2018.
SideKick Solo, Feeding Tube Stand, http://sidekicksolo.com/sidekick-solo/, Accessed on Nov. 6, 2018.

* cited by examiner

LEFT FLOW

NO FLOW

FEEDING SET AND ENTERAL FEEDING PUMP ASSEMBLY

TECHNICAL FIELD

This invention relates generally to pumps that are used to deliver fluids to patients, and more particularly, enteral feeding pumps and accessories therefor.

BACKGROUND

Enteral feeding pumps are used to deliver a controlled amount of water or fluid nutrition to patients who are unable to eat, such as through a patient's nose or mouth. To advance the fluid to a patient, the pumping system may include a positive displacement pump, such as a peristaltic pump that advances the fluid through disposable tubing. The tubing sets typically connect the containers or bags of fluid to the pump and then the patient.

Enteral feeding pumps typically employ either a rotary or a linear pump. The pumps generally have a housing with a motor therein and an actuator device, such as a pump rotor, roller, or platens used to advance the fluid through the tubing. Although enteral feeding pumps are usable for a substantial amount of time, the feeding sets or tubing used with such pumps are typically changed daily. When the feeding sets are changed, patients are at an increased risk of errors and accidents pertaining to those feeding sets. Thus, any improvement to this daily activity can improve patient outcomes.

It has now been found that a feeding set may be provided for placement at least partially within an enteral feeding pump. The feeding set includes a dispensing control valve sized for placement within the enteral feeding pump and configured to releasably engage a first retention portion of the enteral feeding pump, a peristaltic tubing element fluidly connected to an exit of the dispensing control valve, the peristaltic tubing being elastomeric, and an attachment mechanism configured to releasably engage a second retention portion of the enteral feeding pump. The peristaltic tubing element is sized to be placed under tension and to be retained with respect to the pump via tension when the dispensing control valve engages the first retention portion of the enteral feeding pump and the attachment mechanism engages the second retention portion of the enteral feeding pump. Via this approach, the enteral feeding set is firmly fixed with respect to the pump when in use, but can be removed and replaced quickly and easily.

Also contemplated in some embodiments is an enteral feeding pump assembly that includes a feeding set as described above and an enteral feeding pump. The enteral feeding set is sized with respect to the pump to allow retention of a tube of the enteral feeding set via tension as discussed above. In still other embodiments are contemplated a method of providing an enteral feeding pump for use with a nutritional liquid and feeding set, the method comprising attaching a first portion of a feeding set to a panel of the pump via at least one first retainer of a dispensing control valve that is attached to a first edge of the panel, and attaching a second portion of a feeding set to the panel via a second retainer that is associated with a second edge of the panel. The panel may be an internal panel of the pump and the method may include opening a pump door to expose the internal panel and closing the pump door.

BRIEF DESCRIPTION OF THE DRAWINGS

Disclosed herein are embodiments of systems, apparatuses and methods pertaining to the feeding set and enteral feeding pump. This description includes drawings, wherein.

Figure 1A:
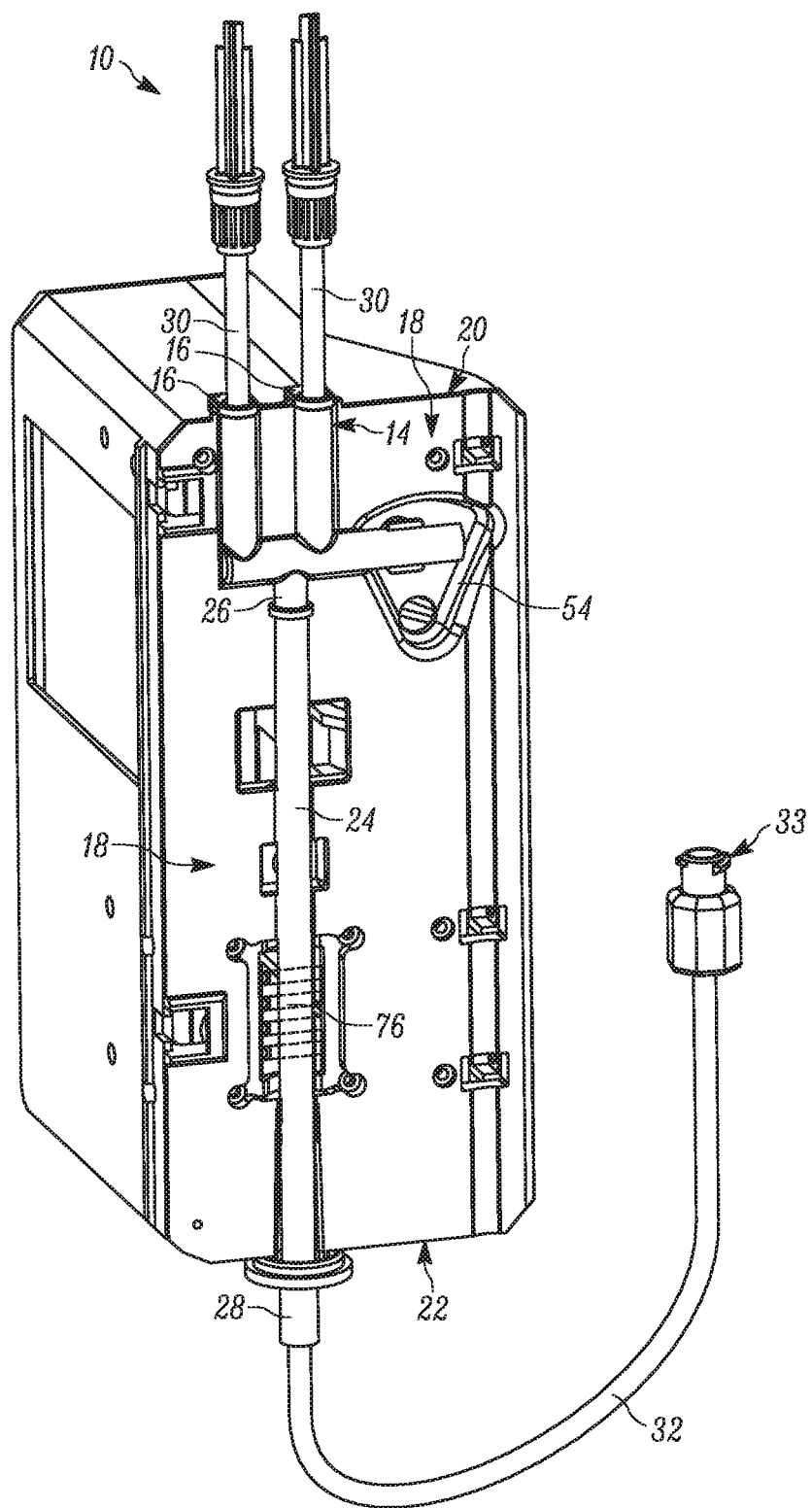
FIG. 1A is perspective view of a feeding set and a portion of a pump with a pump door and the actuator device removed therefrom.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses and methods are provided herein useful to provide fluid nutrition and hydration to an individual. In some embodiments, an enteral feeding pump is used with a feeding set that has an attachment mechanism to associate the feeding set with the enteral feeding pump. For example, the feeding set, in some configurations, includes a dispensing control valve with one or more clips or hooks extending therefrom, where the clip is configured to engage with a portion of the pump housing of an enteral feeding pump, a peristaltic tube or tubing element that is elastomeric and fluidly connected to an exit of the dispensing control valve, and a retention disk configured to engage another portion of a pump housing. In one illustrative embodiment, the clips and the retention disk engage portions of a panel of the pump housing, such as opposing edges of an internal panel to secure the feeding set to the pump. By one approach, the peristaltic tubing element pulls the retention disk and the dispensing control valve toward one another when separated from one another a distance slightly larger than the length or width of the internal panel. For example, the peristaltic tubing may pull the retention disk upward into engagement with a lower edge of the internal panel once the clips of the dispensing control valve are hooked onto an upper edge of the internal panel, or vice versa (i.e., the peristaltic tubing may pull the clips of the dispensing control valve into engagement with an upper edge of the internal panel once the retention disk is engaged with the lower edge of the internal panel).

In this manner, the feeding set retains its connection with the internal panel of the enteral feeding pump via the attachment mechanism of the feeding set, including, for example, at least one clip and a retention disk. Further, this secure attachment maintains the connection between the feeding set and the pump even when the housing door is open or removed from the pump. This is particularly helpful when a nurse or attendant is changing the hydration or nutrition containers attached to the feeding set, visually inspecting an installed feeding set, and changing or setting up a feeding set. Indeed, while the pump door also helps secure the feeding set in position (and also provides protection for the feeding set during operation of the pump), the feeding set typically remains securely attached to the pump even when the door is open or removed from the pump via the connection mechanisms described herein.

In addition to the peristaltic tubing element disposed between the dispensing control valve and the retention disk, the feeding set also typically includes a tubing element for fluidly connecting at least one bag of fluid to the dispensing control valve and a patient tubing element configured to be fluidly connected to the first, peristaltic tubing element and having a patient coupling fitted thereto. As discussed below, though the peristaltic tubing element is typically of a different thickness or material from the other tubing elements, these other tubing elements may nonetheless be formed of the same material, as compared to the peristaltic tubing element.

The attachment mechanisms described herein can be employed with a number of differently configured dispensing control valves. Further, the design and selection of the dispensing control valve can be tailored to the needs of the patient. For example, the dispensing control valve may have ports for both feed and flush activities, i.e., for both liquid nutrition and hydration. In other configurations, a patient may not require one or the other of the ports, and therefore, the dispensing control valve, in other configurations, may include either only a feed port, or, in other configurations, only a flush port.

Whether the dispensing control valve has a single port or two ports, it typically has at least one attachment clip associated with each of the ports. By some approaches, the clip has a hook-like configuration that extends from an upper surface of the dispensing control valve.

In some illustrative embodiments, the dispensing control valve has a plunger positioned partly therein. In operation, the plunger is employed to control or restrict fluid flow through the dispensing control valve. To facilitate such control, the plunger has one or more gaskets (e.g., three gaskets) in some configurations. Further, in between at least some of these gaskets, the plunger may have a narrower or slotted portion that permits fluid to move therebetween. For example, by one approach, the plunger includes multiple narrow portions that have a smaller diameter as compared to the gaskets thereof. In operation, the smaller diameter portion permits fluid to move between the gaskets. In one illustrative configuration, a plunger for use with a dispensing control valve with both feed and flush ports has three gaskets, and the plunger is reciprocable between a feed configuration, a flush configuration, or a no-flow configuration based on the position of the gaskets, which are moved from position-to-position via a grip that is configured to mate with a knob on a reciprocating arm rotatably attached relative to a portion of the pump housing, such as an internal panel. Having a plunger with three gaskets associated therewith, permits the dispensing control valve to have a no-flow, a feed flow, and a hydration fluid flow configuration merely by moving the plunger in a lateral manner within a main channel of the dispensing control valve.

In one illustrative embodiment, the dispensing control valve includes a feed port and/or a flush port, a main channel, and an exit port. As used herein, the ports are sized and configured to received therein or extend into the tubing elements, such as the peristaltic tubing element or the tubing element(s) that connect containers of fluid nutrition or hydration. Further, in such a configuration, the plunger resides in the main channel and has three gaskets, which are reciprocally movable between a feed configuration, a flush configuration, or a no-flow configuration based on the position of the gaskets. In this manner, the plunger may move to permit or restrict the flow from tubing attached to an inlet of the dispensing control valve. In addition, the plunger and gaskets associated therewith are moved from position via a grip of the plunger that is configured to mate with a knob on a reciprocating arm rotatably attached to the internal panel.

In some illustrative configurations, the pump housing, such as the internal panel, has a number of elements that facilitate the attachment of the feeding set, movement of the plunger within the dispensing control valve, engagement of a series of keys or platens with the peristaltic tubing, and/or proper seating of the peristaltic tubing, among other aspects. To that end, the internal panel, in some configurations, includes a pie-shaped depression configured to receive or house the reciprocating arm with the knob associated therewith and/or an arcuate depression partially extending from the first edge to the second edge thereof configured to seat at least a portion of the first tubing element therein. In some embodiments, the internal panel has a rectangular opening therein through which a plurality of keys extend that are configured to sequentially advance to move the fluid through the first, peristaltic tubing. In operation, the plurality of keys may sequentially advance and pinch the peristaltic tubing against the closed door of the pump housing to advance the fluid therein.

Further, to facilitate attachment of the feeding set thereto, in one illustrative embodiment, the internal panel has at least one of an extension and or a depression associated with an edge of the internal panel that is configured to mate with the feeding set. By one approach, the internal panel has at least one of an extension and/or a depression on opposite edges thereof that are configured to mate with one of the dispensing control valve (for example, via the clip) or the retention disk. As used herein, the internal panel may be partially or wholly internal to the remainder of the pump housing. In one illustrative embodiment, a majority of the internal panel is internal to a remainder of the pump housing and the internal panel has upper and/or lower portions that extend slightly outside a remainder of the pump housing.

As noted, the internal panel may have an extension and/or depression on opposite sides thereof that assist with mating the feeding set to the panel. Indeed, in some configurations, the retention disk has geometry, for example, an outer ring and/or a depression or groove that is configured to mate the retention disk with the internal panel, which may include geometry to facilitate the engagement as well. As noted above, the peristaltic tubing element also may be elastomeric such that the geometry of the dispensing control valve and retention disk are brought into contact with opposing edges of the internal panel.

By one approach, a lower attachment mechanism has a central disk, a tapered portion on one side of the central disk and a collar on the other side of the central disk. In some embodiments, the lower attachment mechanism or retention disk includes or has a tapered section attached thereto that is configured to connect to tubing by extending therein, a flange, and a collar configured to connect to tubing by receiving an end of a tubing segment. More particularly, the retention disk may include a tapered section that connect to the first or the third tubing element by extending therein and a collar opposite the tapered section that is configured to receive the other of the first or the third tubing element. Further, in some configurations, the flange of the retention disk comprises an outer ring and a depression or groove between the outer ring and a center wall of the disk, where the outer ring and depression are configured to mate with geometry of the internal panel. By one approach, the retention disk has an outer ring disposed on a first side thereof facing the tapered section, wherein the outer ring defines a flange depression between the tapered section and the outer ring. Further, in such a configuration, the internal panel may have at least one of an extension and/or a depression that is configured to mate with the outer ring or the flange depression to mate the retention disk with the internal panel via the upward force on the retention disk resulting from the elastomeric material of the first tubing element. In addition, the retention disk, in some configurations has an outer ring with an angled surface that facilitates engagement of the first side of the flange of the retention disk with the second edge of the internal panel.

A linear, peristaltic enteral feeding pump, such as those described herein, also generally includes a pump motor within a pump housing and a pump door that captures the internal panel at least partially within the pump housing. By one approach, the enteral feeding pump has a pump door hingedly attached to the housing body, where the pump door moves from an open position to a closed position to further retain the internal panel securely within the housing and protect the feeding set during use thereof. Further, the feeding sets described herein may retain the feeding set relative to the internal panel (and, by extension, the pump), whether the pump door is in the closed or open position, via the attachment mechanism, such as the at least one clip and the retention disk.

Figure 1B:
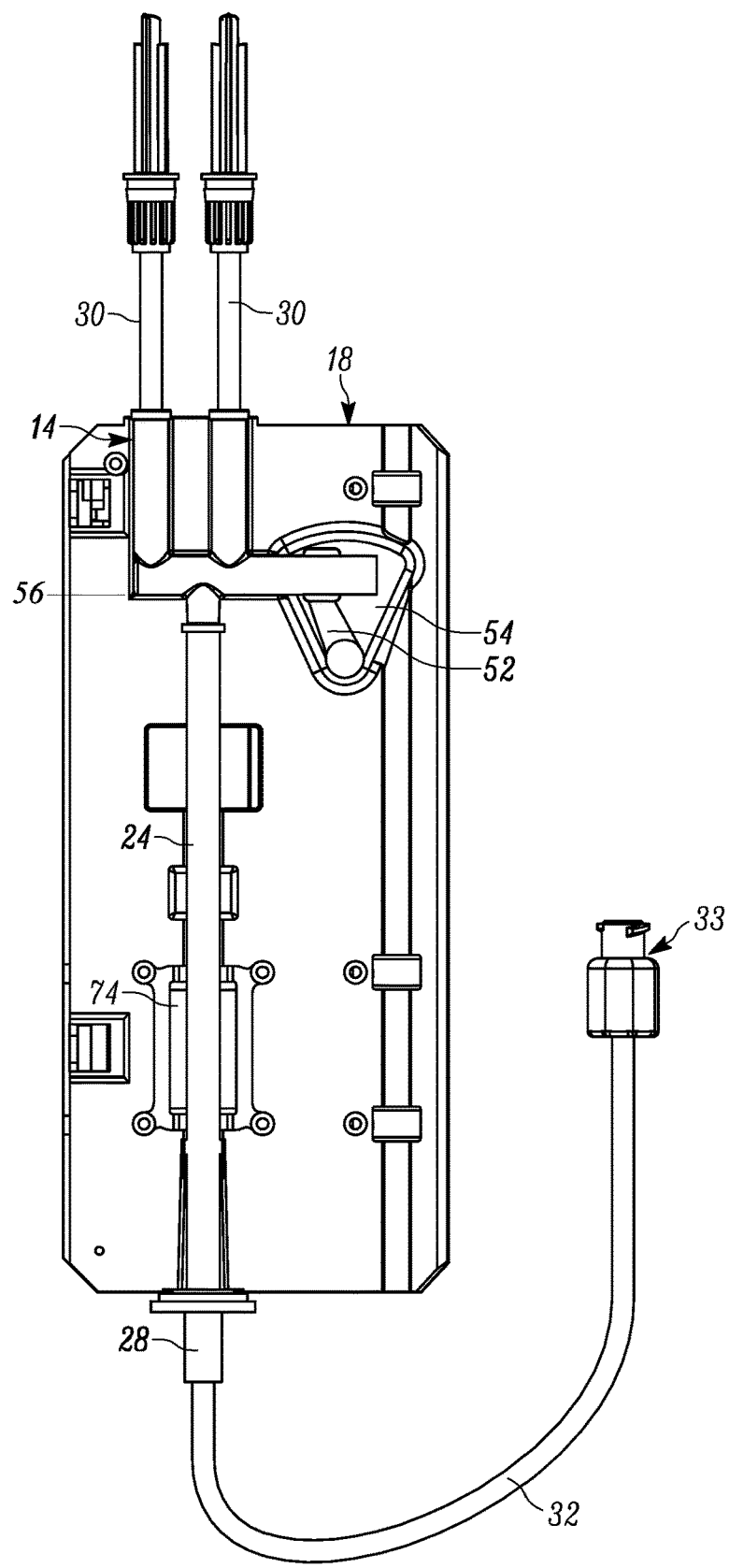
FIG. 1B is front elevational view of a feeding set connected to a portion of a pump.

As shown in FIGS. 1A and 1B, a feeding set 10 has an attachment mechanism for use in selectively attaching the feeding set 10 to an enteral feeding pump 12 (see, e.g., FIG. 4) or a portion thereof, such as an internal panel 18 (see, e.g., FIG. 1A). In one configuration, the feeding set 10 includes a dispensing control valve 14, a first tubing element 24, a retention disk 28, one or more second tubing elements 30, and a third tubing element 32. In the embodiment illustrated in these Figures, the dispensing value 14 has at least one clip 16 or hook extending therefrom, where the clip 16 is configured to engage a portion of the enteral feeding pump 12, such as a first edge 20 of an internal panel 18 thereof. In some embodiments, the first tubing element 24 is elastomeric and has peristaltic capabilities such that, for example, the tubing is thin and flexible enough to permit platens or keys 76 (described below) to move the fluid in the feeding set 10 when the pump is in use.

Figure 9A:
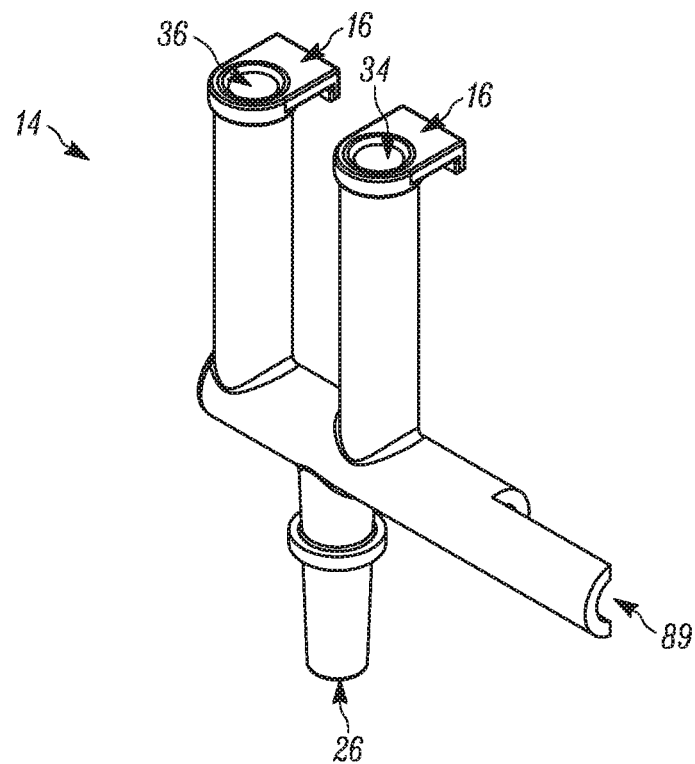
FIG. 9A-9C are perspective views of different valves useful in with the feeding sets.
Figure 9B:
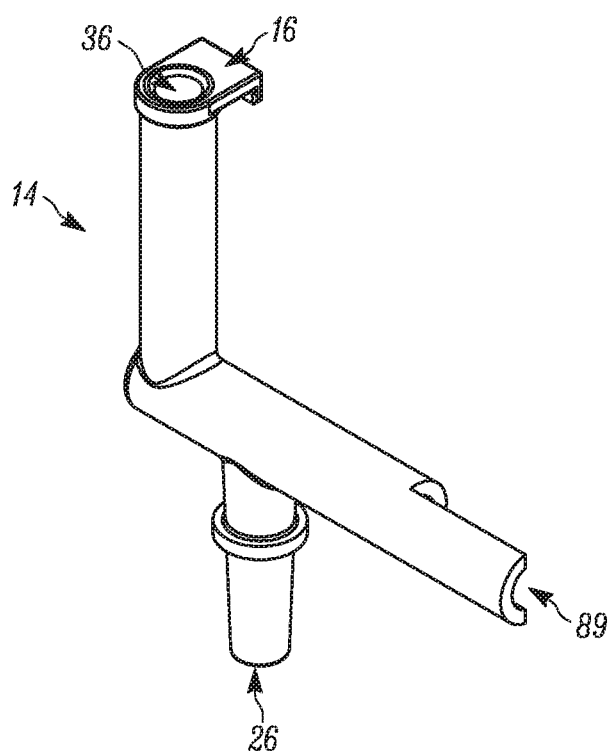
Figure 9C:
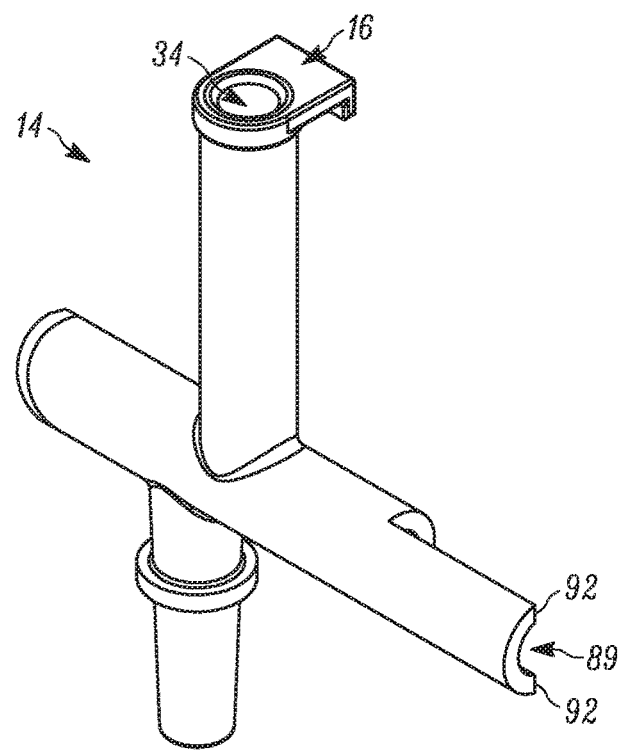
Figure 10:
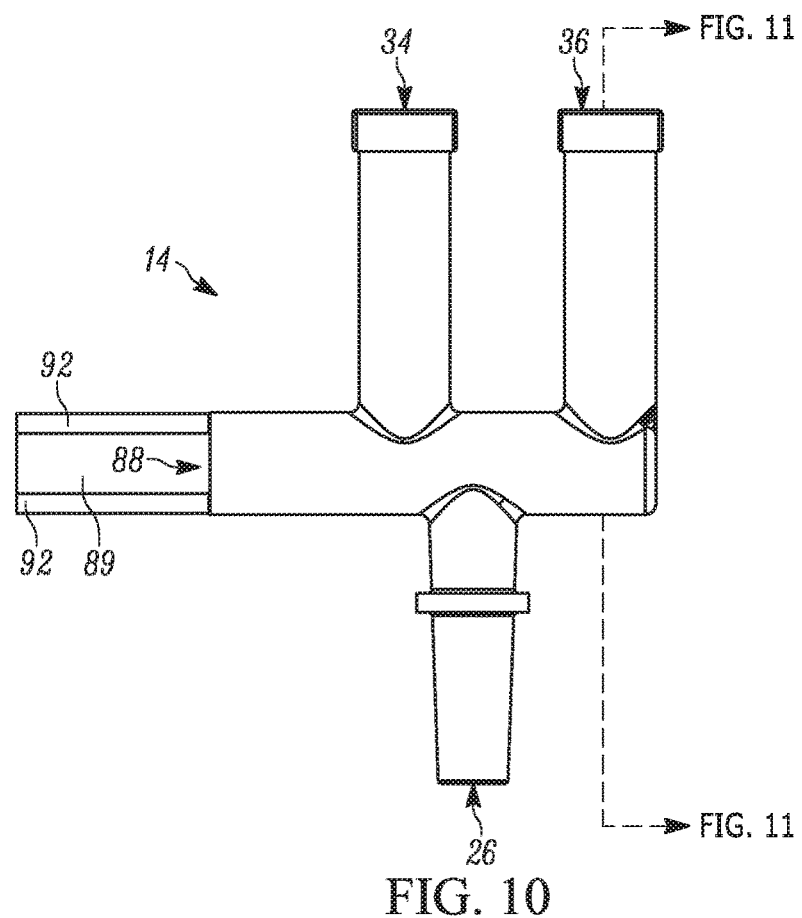
FIG. 10 is a rear elevational view of the valve of FIG. 9A.
Figure 15A:
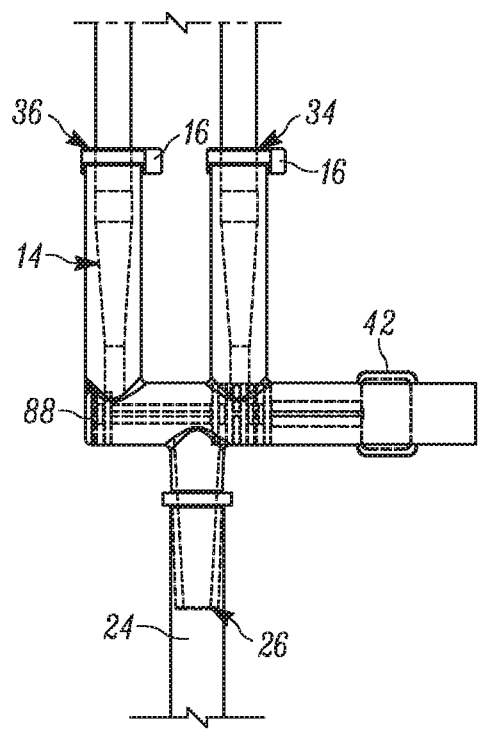
FIGS. 15A-15C are front elevational views of different valves and plungers associated therewith.
Figure 15B:
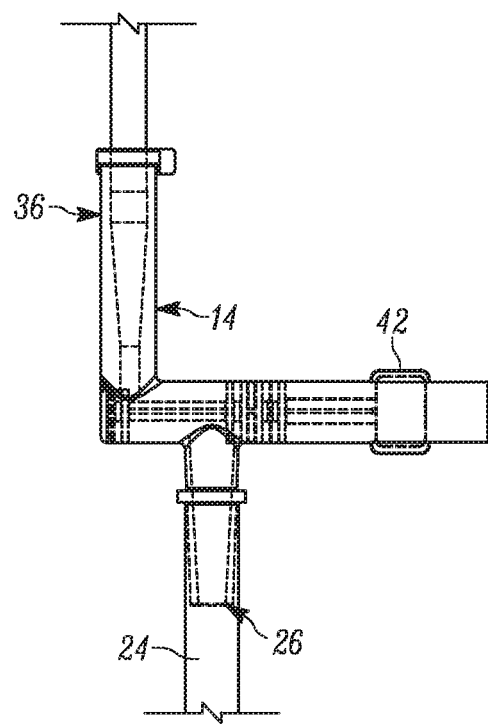
Figure 15C:
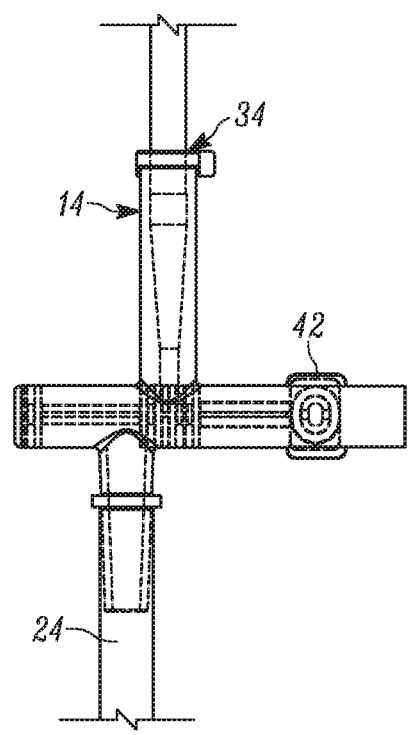
Figure 16:
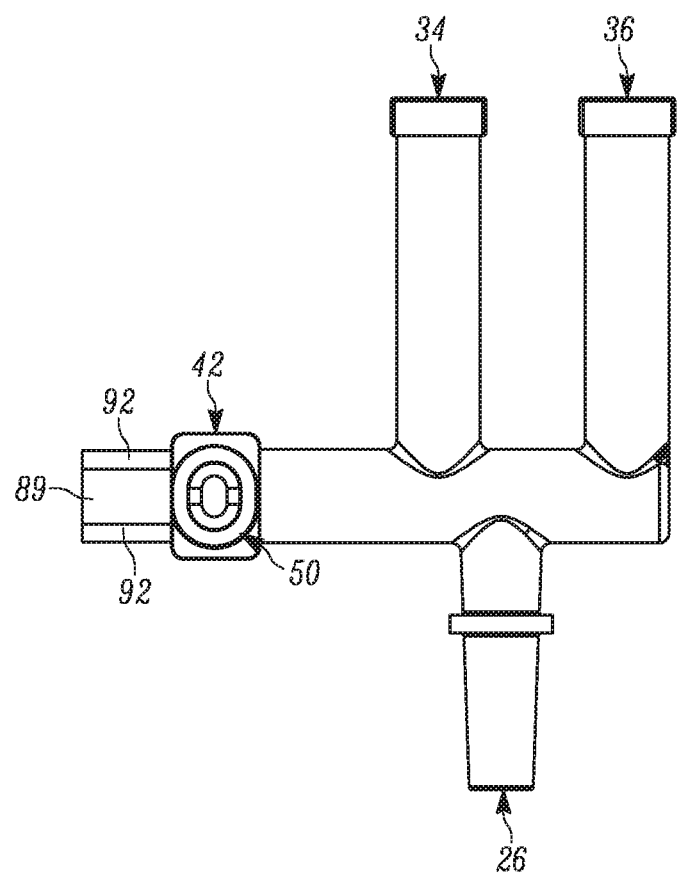
FIG. 16 is a rear elevational view of the valve of FIG. 9A with a plunger associated therewith.

As illustrated, for example, in FIGS. 15A-15C, the peristaltic, first tubing element 24 fluidly connects to an exit 26 of the dispensing control valve 14 (see also FIGS. 9A-9C). In some embodiments, the retention disk 28 is configured to engage a second edge 22 of the internal panel 18, as shown in FIG. 1A. Further, the peristaltic tubing 24 typically pulls the retention disk 28 upward into engagement with the second edge 22 of the internal panel 18, such that the feeding set 10 retains its connection with the internal panel 18 of the enteral feeding pump 12 via the at least one clip 16 and the retention disk 28.

Returning to FIG. 1A, the feeding set 10 also typically includes one or more second tubing elements 30 for fluidly connecting the feeding set 10 to at least one container or bag filled with fluid. More specifically, the second tubing element 30 typically connects with the fluid container at a first end and to the dispensing control valve 14 at a second end thereof. In addition, the third tubing element 32 is configured to be fluidly connected to the first tubing element 24 via the retention disk 28 and also has a patient coupling 33 fitted thereto that permits the feeding set 10 to be in fluid communication with the patient.

Figure 6:
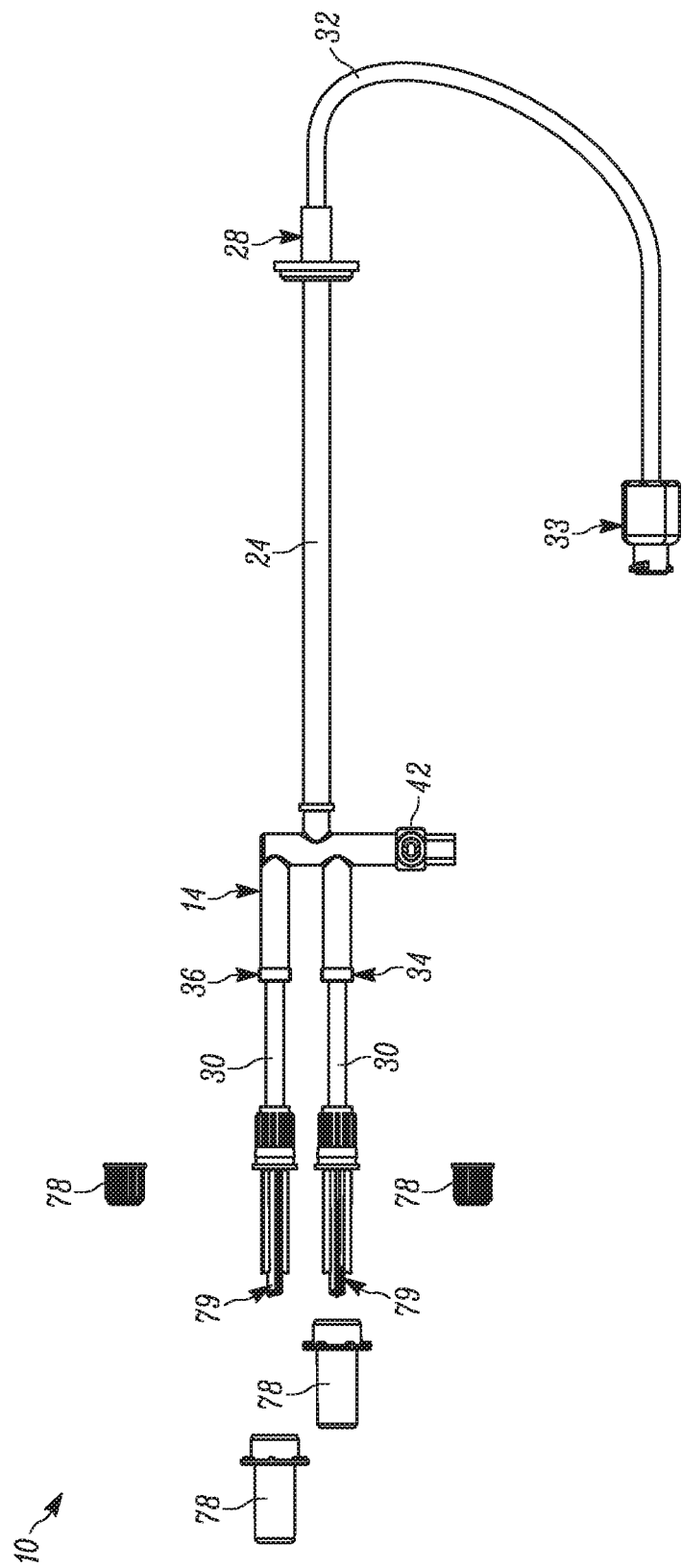
FIG. 6 is an exploded view of a feeding set.
Figure 7:
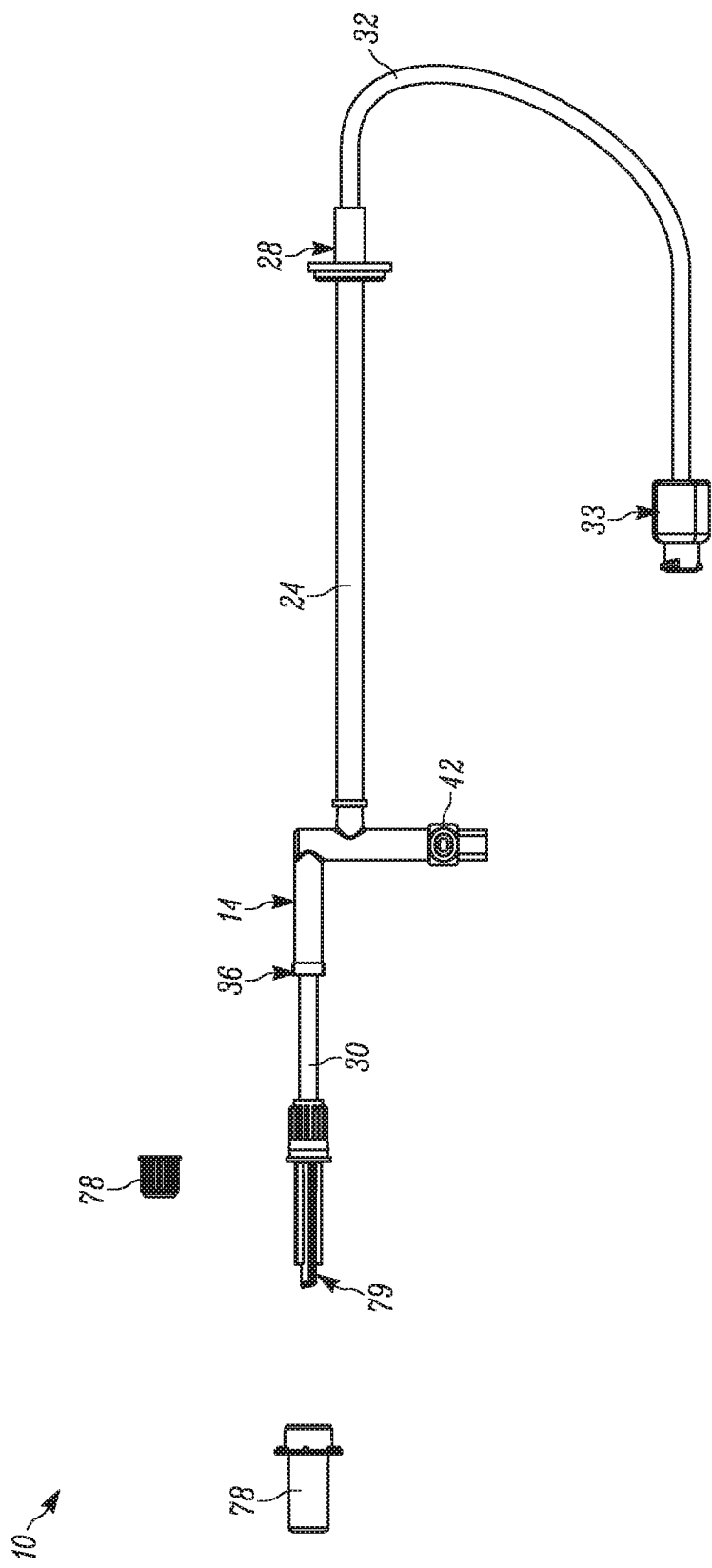
FIG. 7 is an exploded view of another feeding set.
Figure 8:
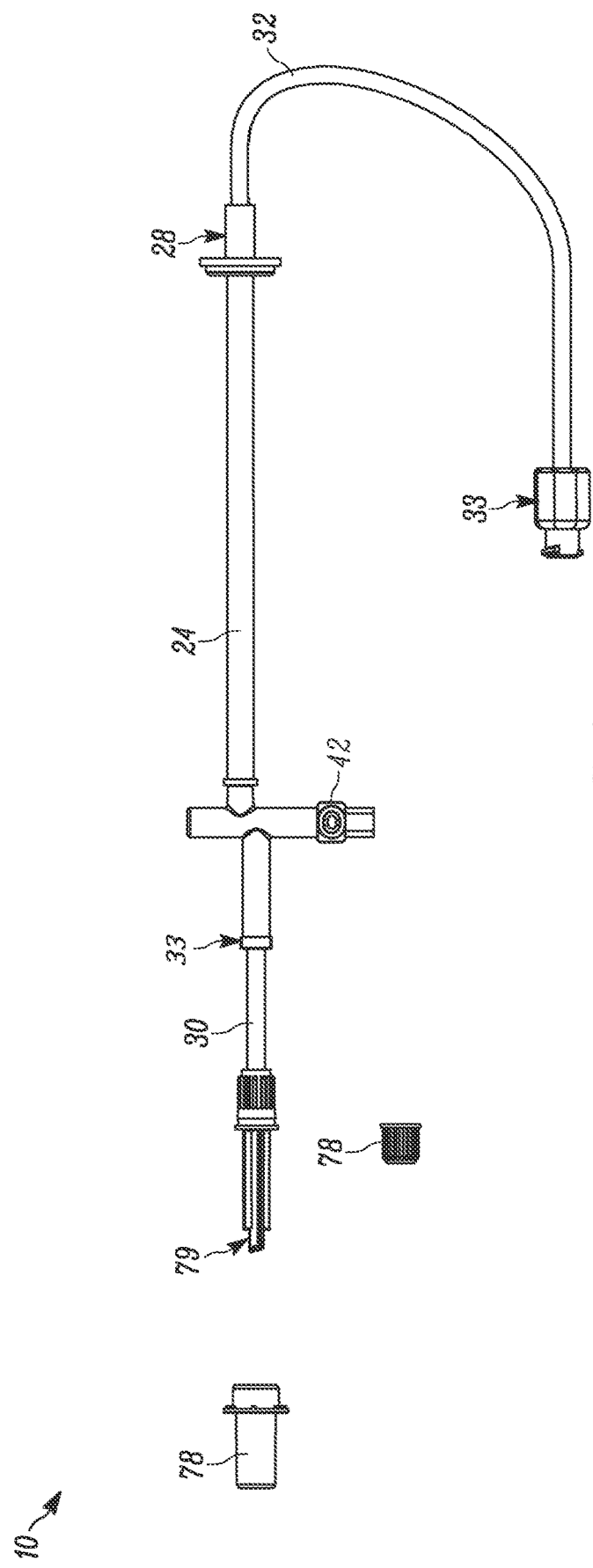
FIG. 8 is an exploded view of another feeding set.

FIGS. 6-8 show three illustrative examples of the dispensing control valve 14. In one illustrative configuration, shown in FIG. 6, the dispensing control valve 14 has a feed port 36 for connection to fluid nutrition and flush port 34 for connection to fluid hydration. In the illustrative configuration of FIG. 7, the dispensing control valve 14 includes a feed port 36 but not a flush port 34, whereas in the illustrative configuration of FIG. 8, the dispensing control valve 14 includes a flush port 34, but not a feed port 36.

Figure 2A:
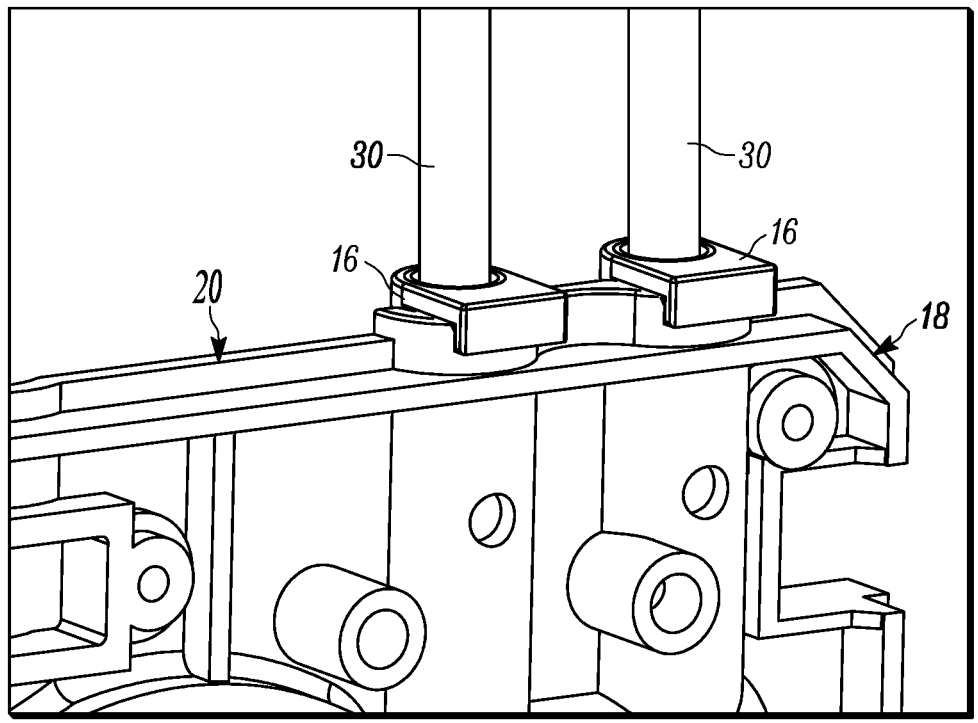
FIG. 2A is a perspective view of a connection mechanism between a portion of a feeding set and an internal panel removed from a remainder of a pump housing.
Figure 2B:
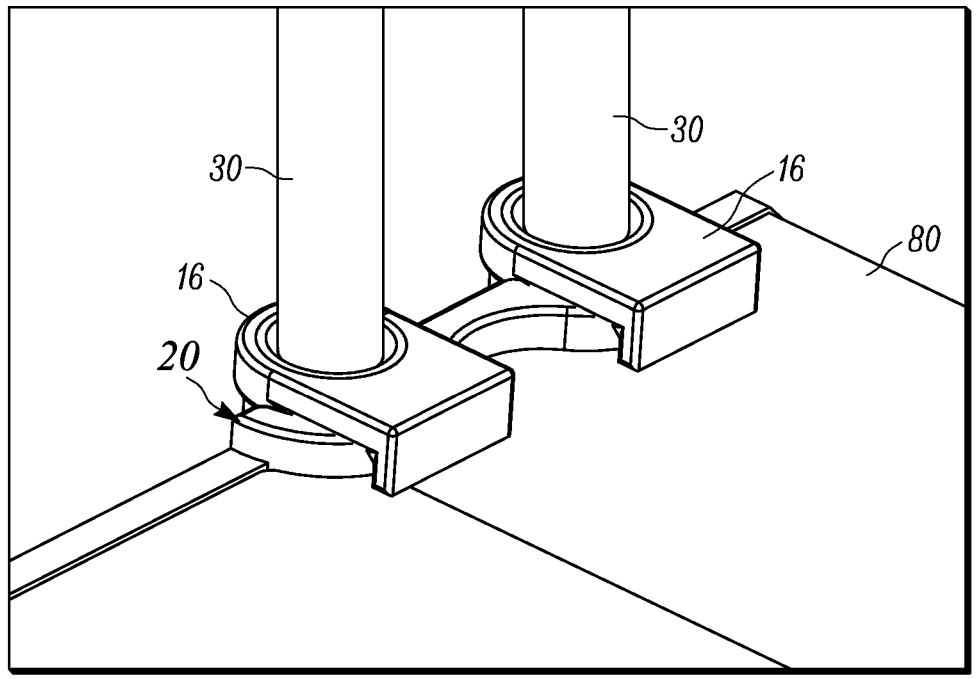
FIG. 2B is another perspective view of a connection mechanism.
Figure 11:
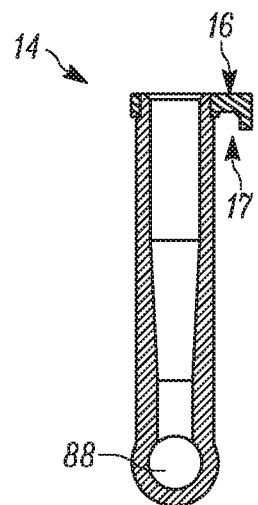
FIG. 11 is a cross sectional view of the valve of FIG. 10 along line 11-11.

FIGS. 9A-9C also show the various port configurations of the dispensing control valve 14. As shown, the feed and flush ports 34, 36 of the dispensing control valve 14 typically have an attachment clip or hook 16 associated therewith, as described further below. By one approach, the feed port 36 has first attachment clip 16 associated therewith and the flush port 34 has a second attachment clip 16 associated therewith. In some illustrative configurations, the attachment clip 16 has hook-like configuration that extends from an upper surface of the dispensing control valve 14 and depends downward in the general direction of the remainder of the dispensing control valve 14. FIG. 11 illustrates how one exemplary hook 16 may form a channel 17 that receives a portion of the pump, such as a portion of an edge of the internal panel 18. Further, FIG. 2A, which illustrates the internal panel 18 removed from a remainder of the pump housing 80, and FIG. 2B, which illustrates the internal panel 18 associated with a portion of a pump housing 80, illustrate the manner in which the clip 16 may extend over a portion of the upper edge of the internal panel 18.

In operation, the dispensing control valve 14 fluidly engages with the first tubing element 24 and the second tubing element(s) 30 connected therewith. Each segment of the second tubing element 30 attached to the dispensing control valve 14 typically has a spike attachment mechanism 79 for coupling the feeding set 10 to a container or bag of fluid nutrition or hydration. FIGS. 6-8 illustrate two different versions of a spike cap 78 that may be incorporated into a feeding set 10 to cover or cap the spike attachment mechanism 79. By some approaches, the spike cap 78 and the spike attachment mechanism 79 are mated together via snap-fit, friction-fit, threads, or other suitable securement mechanisms. While some feeding sets 10 may include more than one spike cap 78 per port, the feeding set 10 typically has a single spike cap 78 for each spike attachment mechanism 79.

Figure 12:
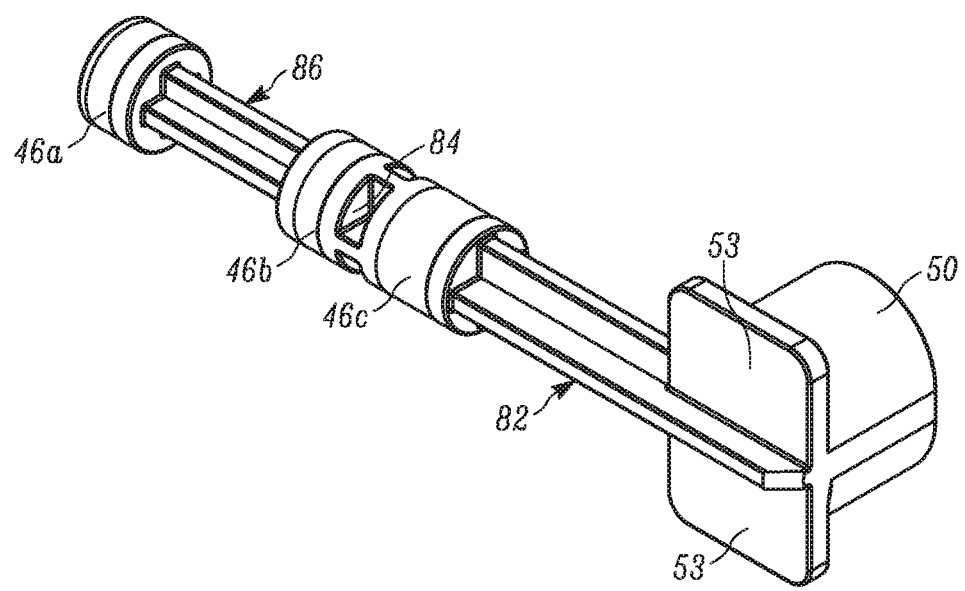
FIG. 12 is a perspective view of a plunger usable with the valves of FIGS. 9A-9C.
Figure 13:
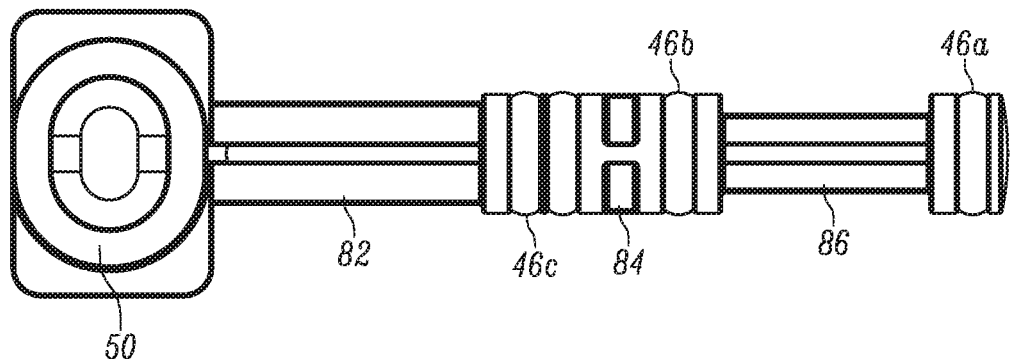
FIG. 13 is a rear plan view of the plunger of FIG. 12.
Figure 14:
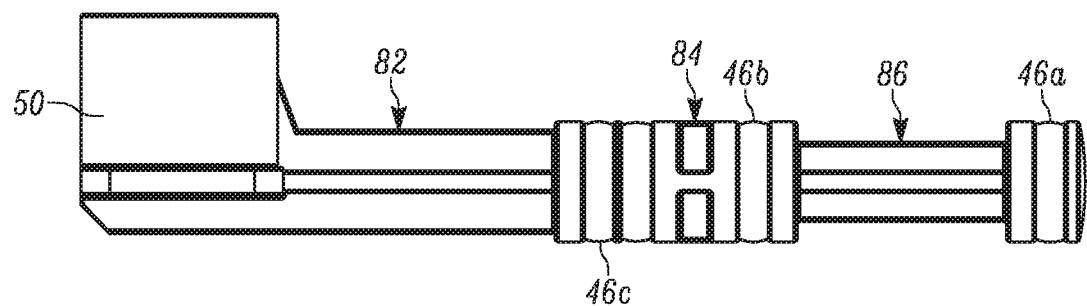
FIG. 14 is a top plan view of the plunger of FIG. 12.

As indicated above, the dispensing control valves, such as those illustrated in FIGS. 6-8, operate with a plunger disposed partially therein. More specifically, a portion of the plunger 42 resides in a main channel 88 (see, e.g., FIG. 11) during use of the feeding set 10. FIGS. 12-14 illustrate various view of an exemplary plunger 42. The plunger 42 operates to open and close the one or more ports 34, 36 of the dispensing control valve 14 to restrict or permit fluid flow therethrough. To that end, the dispensing control valve 14 includes a plurality of gaskets 46a, 46b, 46c that are configured to restrict the flow of fluid through the dispensing control valve 14. Further, the plunger 42 is configured to move (and thereby move the gaskets 46a, 46b, 46c) along the channel 88 that is connected to the inlets or feed and flush ports 34, 36 and the exit 26.

As shown in FIGS. 12-14, the plunger 42 typically includes multiple narrow portions 82, 84, 86. The narrow portions 82, 84, 86 generally have a smaller diameter than the gaskets 46 and/or cut outs or slits therein, as shown in the narrow portion 84 in FIG. 12. In one illustrative approach, the narrow portion 86 permits the fluid to flow along that portion of the plunger in between the adjacent gaskets 46a, 46b. In operation, the plunger 42 and gaskets 46a, 46b, 46c can be laterally moved within the main channel 88 of the dispensing control valve 14. To that end, the plunger 42 also typically includes a plunger grip 50 that extends outward of the c-shaped channel 89 when the plunger 42 is partly disposed within the dispensing control valve 14. The orientation of the plunger grip 50 permits it to be associated with a portion of the feeding pump 12. Further, the main channel 88 may have an extension portion with a groove or c-shaped channel 89 within which a portion of the plunger 42 opposite the grip 50 may reside. By one approach, the c-shaped channel 89 has top and bottom flat surfaces 92. In operation, the extensions 53 of the plunger 42 (FIG. 12) adjacent the plunger grip 50 are able to abut or slide along the flat surfaces 92 of the c-shaped channel when the plunger 42 is moved into different positions within the dispensing control valve 14 (such as the flush port 36 open configuration (i.e., left flow or feed open) shown in FIG. 5A, the all closed or no flow configuration shown in FIG. 5B, or the flush port 34 open configuration (i.e., the right flow or flush open configuration) shown in FIG. 5C).

Figure 5A:
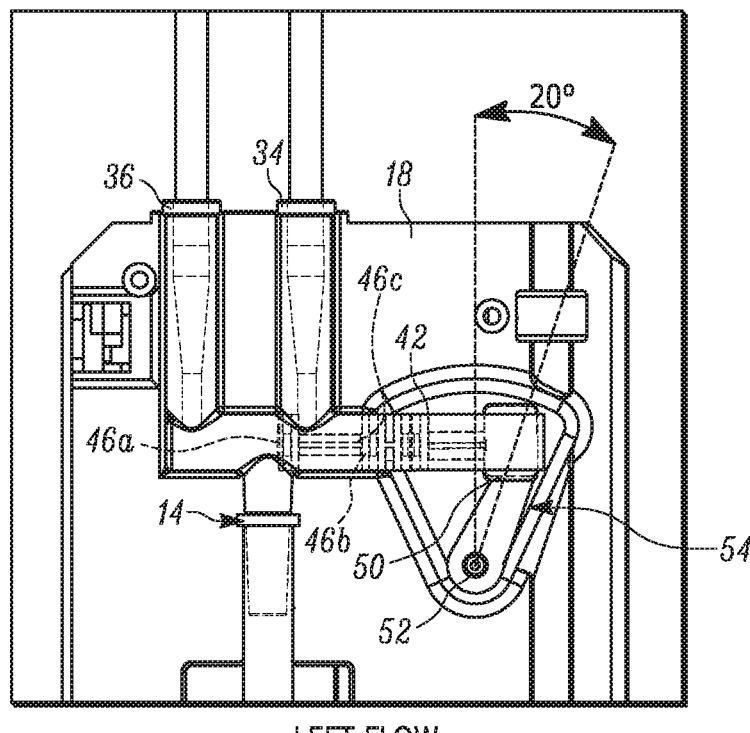
FIGS. 5A-5C are front elevational views of a portion of an internal panel and a dispensing and control valve with the plunger in different arrangements.
Figure 5B:
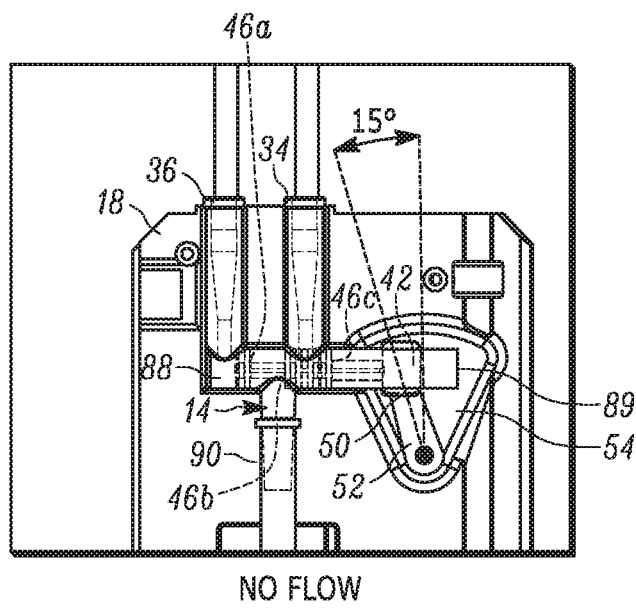
Figure 5C:
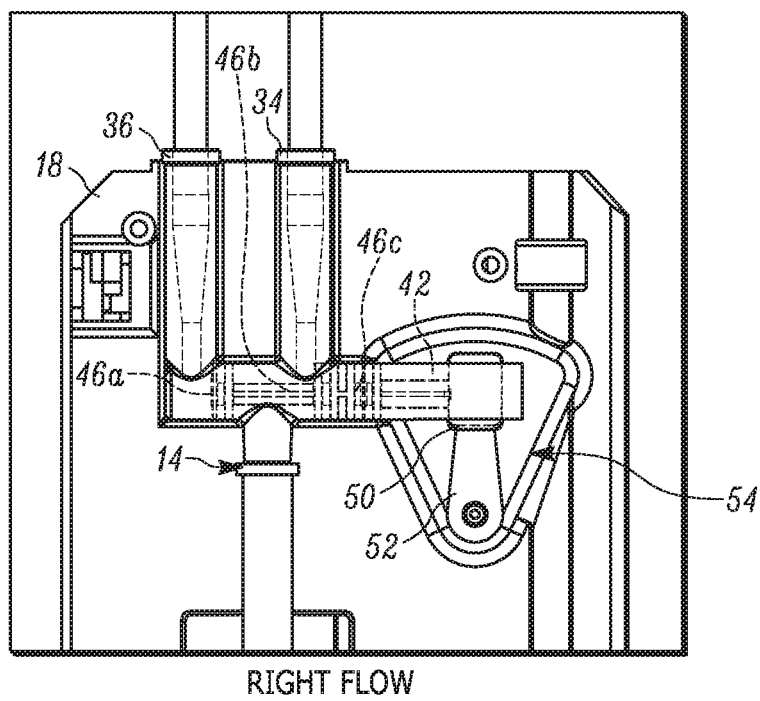

More particularly, FIGS. 5A-5C illustrate the plunger 42 within the dispensing control valve 14 in a variety of positions such that the gaskets 46 prevent or permit the flow of fluid therein. For example, FIG. 5A illustrates the grip 50 of the plunger 42 moved outward or away from the ports 34, 36. Accordingly, FIG. 5A illustrates the dispensing control valve 14 with the plunger 42 in the feed-flow or open position for port 36, and accordingly, the plunger 42 is disposed so that gasket 46a blocks fluid from moving from the port 34, but permits fluid from the port 36 to advance through the discharge channel 90 and to exit 26. Further, FIG. 5B illustrates the grip 50 of the plunger 42 angled leftward or toward the ports 34, 36, and accordingly, the plunger 42 is in the no-flow position of the dispensing control valve 14 such that neither port is open. More particularly, the gasket 46a blocks or prevents fluid in port 36 from advancing through port 36 to the discharge channel 90 and gaskets 46b and 46c in the main channel 88 are disposed on either side of the port 34 so that fluid therein is blocked or prevented from advance through port 34 and into the discharge channel 90 to exit 26. FIG. 5C illustrates the dispensing control valve 14 with the plunger 42 in the flush-flow or open position for port 34. More particularly, the gasket 46a is disposed to block fluid from port 36 from entering the discharge channel 90, but the fluid from the port 34 can freely enter the main channel 88 and the discharge channel 90 to advance to the exit 26 of the dispensing control valve 14. The three configurations of the plunger 42 within the valve 42 are used for different operating phases of the pump.

As indicated above, in one configuration, the feeding set 10 includes a dispensing control valve 14 with a feed port 36 and/or a flush port 34 and a plunger with three gaskets 46a, 46b, 46c, configured such that the plunger 42 is reciprocal between a feed configuration and/or a flush configuration and a no-flow configuration based on the position of the gaskets. In one illustrative approach, the plunger 42 and associated gaskets 46a, 46b, 46c are moved from position to position via the plunger grip 50 that is configured to mate with a knob on a reciprocating arm 52 rotatably attached to the internal panel 18. By one approach, the internal panel 18 has a pie-shaped depression 54 (FIG. 1A) configured to receive, house, and/or permit the reciprocating arm 52 with the knob associated therewith to move within. In some configurations, the internal panel 18 includes an arcuate depression 56 partially extending from the first edge 20 to the second edge 22 that is configured to seat at least a portion of the first tubing element 24 therein. In this manner, the arcuate depression 56 permits the tubing element 24 to be seated, and then, once the pump door 40 is closed the movable keys 76 are able to pinch the peristaltic tubing element 24 in between the keys 76 and the door 40 to advance the fluid therein via peristaltic action.

Figure 3A:
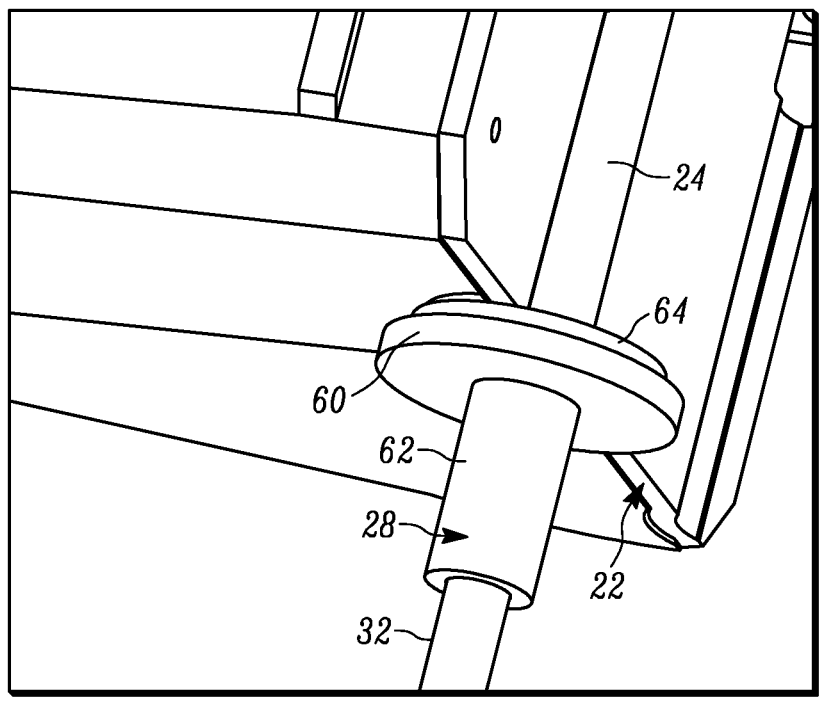
FIG. 3A is a perspective view of a connection mechanism.
Figure 3B:
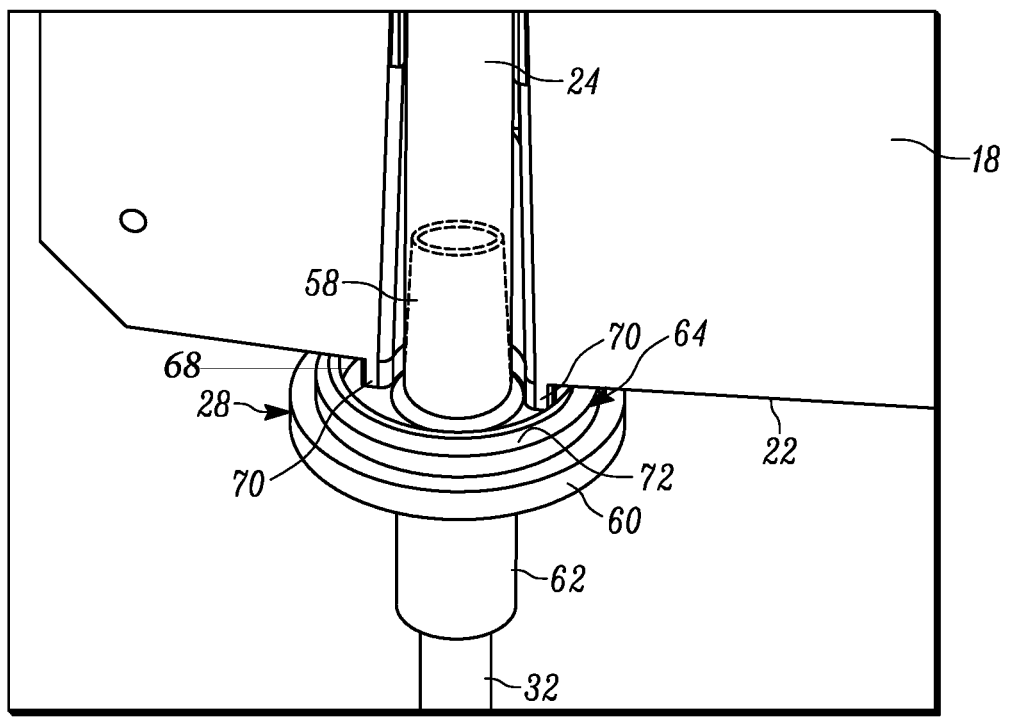
FIG. 3B is another perspective view of the connection mechanism of FIG. 3A.

As noted above, the feeding set 10 is typically attached to the pump via upper and lower connecting elements with an elastic tubing element 24 partially therebetween. The lower connecting element, which may include the retention disk 28, may be configured in a number of manners. For example, FIGS. 3A and 3B illustrate the retention disk 28 engaged with a second portion or edge 22 of the internal panel 18. In one embodiment, the retention disk 28 includes a tapered section 58, a flange 60, and a collar 62. In operation, the tapered section 58 attaches to, or engages with, one of the first tubing element 24 or the third tubing element 32 by having the tapered section extend within the tubing walls. The collar 62 has a diameter that can receive the other of the first tubing element 24 or the third tubing element 32. In the illustrative example shown in FIG. 3B, the tapered section 58 extends into a portion of the first tubing element 24 and the collar 62 receives a portion of the third tubing element 32. Between the tapered section 58 and the collar 62, the retention disk 28 has a flange 60. In one illustrative embodiment, the retention disk 28 has an outer ring 64 on the flange 60 on a side thereof having the tapered section 58. By one approach, the outer ring 64 forms a depression or a retaining groove on the retention disk 28. For example, the flange depression may be formed by the outer ring 64 and the lower wall of the tapered section 58 of the disk 28. In operation, the outer ring 64 of the flange 60 helps retain the retention disk 28 to a second, lower edge 22 of the internal panel 18 such as to prevent it from be accidentally dislodged from the internal panel 18. While the outer ring 64 extends on a side thereof having the tapered section 58, it also could be disposed on a side thereof having the collar 62 if the collar 62 engages the first tubing element 24. In one illustrative approach, the outer ring 64 has an angled surface 72 that facilitates engagement of the retention disk 28 with the second edge 22 of the internal panel 18.

To cooperate with the retaining disk 28, in some embodiments, the internal panel 18 has a cooperating geometry, such as a depression and/or an extension 70 (see, e.g., FIG. 3B). For example, if present the depression and/or extension 70 is present it is generally configured to mate with the outer ring 64 or the flange groove or depression 68 to further secure or mate the retention disk 28 with the internal panel 18 via the upward force on the retention disk 28 resulting from, in part, the elastomeric material of the first tubing element 24.

Figure 17A:
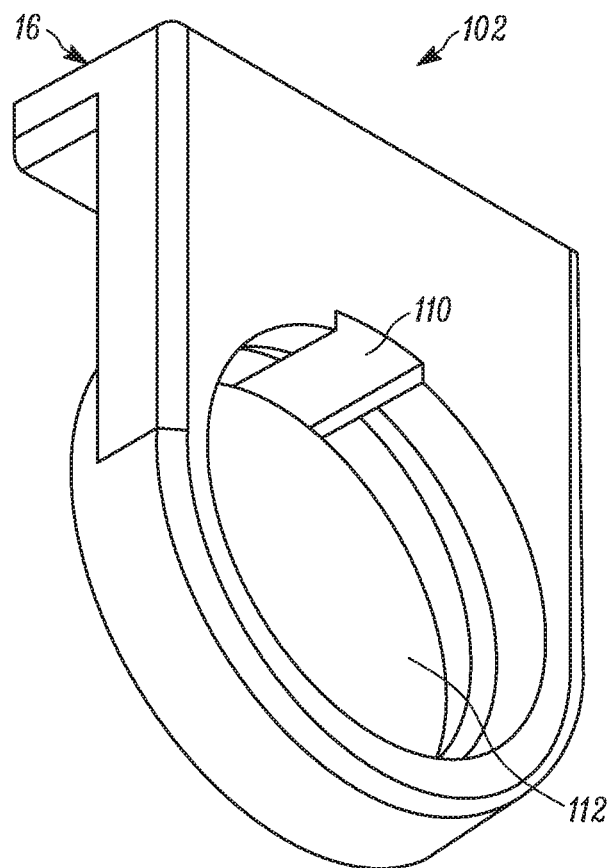
FIGS. 17A and 17B are perspective views of an embodiment of a valve.
Figure 17B:
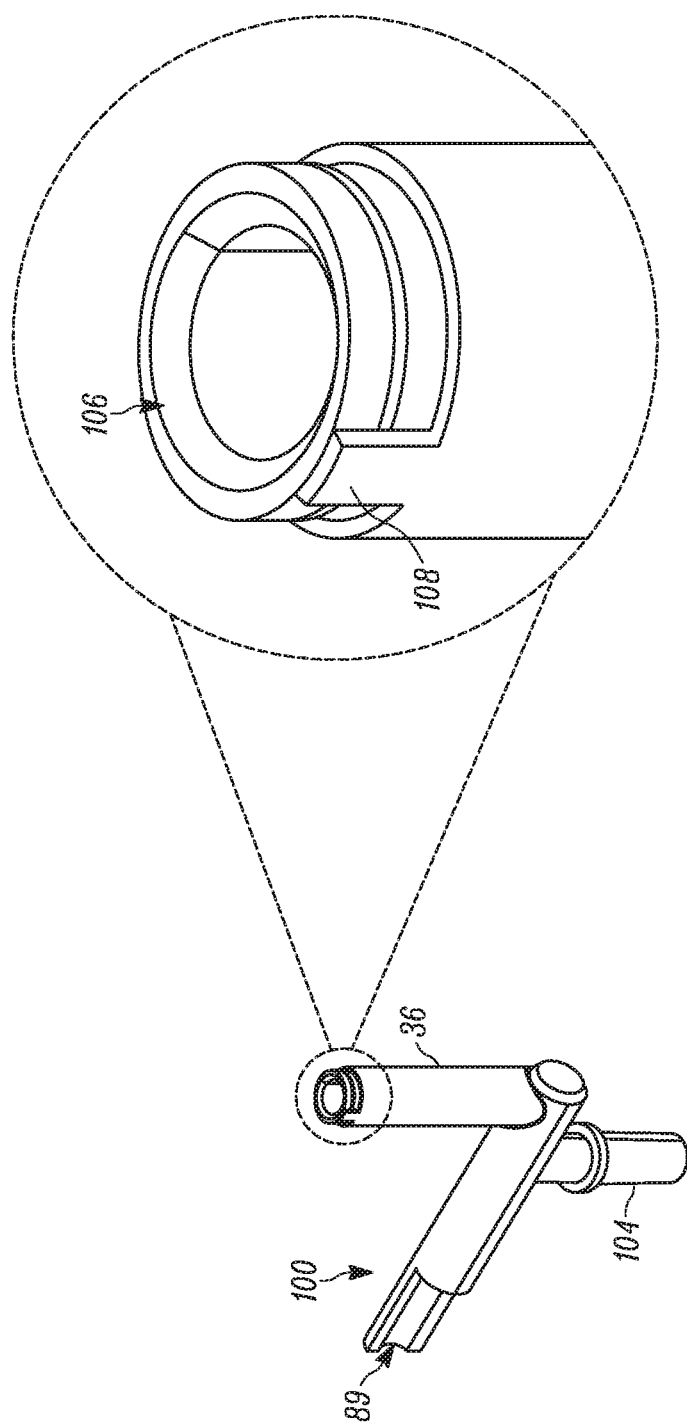

The feeding sets and components thereof described herein may be manufactured in a number of ways. By one approach, the dispensing control valve 14 may be, for example, molded, machined, welded, printed, and a combination thereof, among other manufacturing techniques or processes. In one illustrative approach, a valve body 100 of the valve including the central portion with the channel 88 along with the one or more of the ports (the feed port 36 is illustrated in FIG. 17B) and the discharge channel 104 may be molded in whole or in part. While the valve body 100 may be molded in one or more pieces (which may then secured together), the valve extension(s) 102, shown in FIG. 17A are typically welded onto the inlet collar 106 of the port. To ensure proper directional seating of the valve extensions 102 (e.g., to ensure that the clips 16 extend in the same direction as the c-shaped channel 89), the inlet collar 106 may have a mating feature or projection 108 that may engage with a slot 110 in the valve extension 102. As illustrated in FIG. 17A, the slot 110 extends from the central opening 112 of the valve extension 102. The valve extension(s) 102 are mated to the port(s) 34, 36, by aligning the central opening 112 with the bore or central opening of the port and the slot 110 with the projection 108 and sliding the valve extension 102 onto the collar 106 of the port. Once the valve extension 102 is seated in position, it can be welded, such as sonically welded, onto the dispensing control valve 14. In this manner, once the user has securing the feeding set 10 to the internal panel 18 via the clips 16 of the extensions 102, the dispensing control valve 14 will be in position such that the c-shaped channel 89 and the plunger 42 may cooperate with the portions of the pump that adjust the flow of the fluid through the dispensing control valve 14, such as the reciprocating arm 52.

As noted above, the pump may be a linear peristaltic pump that moves the fluid through the feeding set and to the patient by having keys 76 that press on the peristaltic first tubing element (and against the pump door 40) to move fluid therethrough. By one approach, the internal panel 18 has a rectangular opening 74 therein through which a plurality of keys 76 extend to act on the peristaltic first tubing element 24. In operation, the keys 76 may sequentially extend farther or advance through the opening 74 to compress or pinch a portion of the first tubing element 24 between one of the keys 76 and the pump door 40 to thereby move the fluid. More particularly, the keys 76 compress or pinch the tubing element 24 adjacent the activated one of the keys 76 and the fluid is advanced or pushed forward from the pinched point by the sequential movement of the keys 76.

Figure 4:
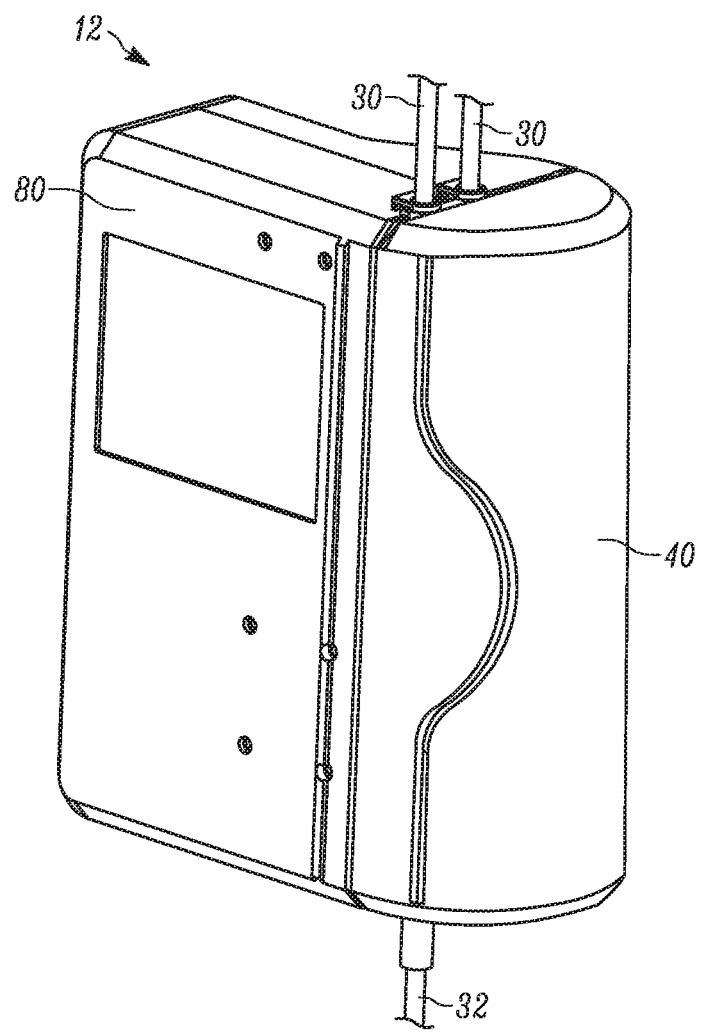
FIG. 4 is a perspective view of the pump with a feeding set secured thereto as shown in FIG. 1A, showing the door in place.

FIG. 4 illustrates the enteral feeding pump 12 with the pump door 40 in the closed position. By one approach, the enteral feeding pump 12 has a pump door 40 that is hingedly attached to a housing body 80, wherein the pump door 40 moves from a first position to a second position, wherein the first position includes the pump door 40 in a closed configuration and the second position includes the pump door 40 in an open configuration, which is used for changing the feeding set 10. Further, the attachment mechanism retains the feeding set 10 into position on the internal panel 18 even when the door 40 is open. This helps prevent the dispensing control valve 14 from being accidentally knocked into the free flow position. Further, in one illustrative configuration, the feeding set 10 remains securely attached to the enteral feeding pump 12 when the pump door 40 is in the first open position via the at least one clip 16 and/or the retention disk 28. More particularly, the feeding set 10 may include a dispensing control valve 14 configured to releasably engage a first retention portion or a first edge of the internal panel 18 of an enteral feeding pump and an attachment mechanism (such as a retention disk 28) configured to releasably engage a second retention portion of the enteral feeding pump such as a second edge of an internal panel 18. Further, between the first retention portion and the attachment mechanism, the feeding set may include a peristaltic tubing element 24 fluidly connected to an exit 26 of the dispensing control valve 14. In operation, the peristaltic tubing may be elastomeric have a predetermined length so that the peristaltic tubing is put under tension when the dispensing control valve engages the first retention portion and the attachment mechanism engages the second retention portion of the enteral feeding pump.

As noted above, the feedings sets 10 are generally replaced each day. Prior to being installed into the pump, the feeding sets 10 generally include one or more spike caps 78 configured to protect and keep the spikes and tubing connectors clean, as shown in FIGS. 6-8. As shown therein, the second tubing element 30, which connects with the fluid nutrition or water when in use, has one or multiple spike caps to protect one end of the second tubing 30.

The feeding sets 10 described herein may be used with a number of enteral feeding pumps, such as the linear enteral feeding pump 12 described herein. In one illustrative method of feeding a patient with an enteral feeding pump for use with a nutritional liquid and feeding set, the method includes opening a pump door thereby exposing an internal panel thereof, attaching a first portion of a feeding set to the internal panel via at least one clip of a dispensing control valve that is attached to a first edge of the internal panel and attaching a second portion of a feeding set to the internal panel via a retention disk that is associated with a second edge of the internal panel, and then closing the pump door thereby permitting plurality of keys to extend through a rectangular opening in the internal panel and move fluid through the first tubing. Further, in some configurations, the valve has a plunger disposed therein, where the plunger is laterally movable therein to open one of a feed line and/or a flush line, or keep the lines/ports in the closed position to prevent fluid from advancing through and being discharged from the dispensing control valve.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A feeding set comprising:
   a dispensing control valve sized for placement at least partially within an enteral feeding pump and configured to releasably engage a first retention portion of the enteral feeding pump, the dispensing control valve having a plunger positioned at least partly therein to selectively control a flow of fluid through the dispensing control valve;

a peristaltic tubing element fluidly connected to an exit of the dispensing control valve, the peristaltic tubing element being elastomeric; and an attachment mechanism configured to releasably engage a second retention portion of the enteral feeding pump;

wherein the peristaltic tubing element is sized to be placed under tension and for said peristaltic tubing element to be retained with respect to the enteral feeding pump via tension when the dispensing control valve engages the first retention portion of the enteral feeding pump and the attachment mechanism engages the second retention portion of the enteral feeding pump.

2. The feeding set of claim 1, wherein the attachment mechanism comprises a retention disk and the peristaltic tubing element pulls the retention disk upward toward the dispensing control valve in an assembled, installed configuration.

3. The feeding set of claim 2, further comprising:
a second tubing element for fluidly connecting the dispensing control valve with at least one bag of fluid; and
a third tubing element configured to be fluidly connected to the peristaltic tubing element, via the retention disk, wherein the third tubing element has a patient coupling fitted thereto.

4. The feeding set of claim 3, wherein the patient coupling comprises a male enfit.

5. The feeding set of claim 1, wherein the dispensing control valve has a clip and the first retention portion of the enteral feeding pump includes a panel or a portion thereof and wherein the clip of the dispensing control valve is configured to engage the panel in an assembled, installed configuration.

6. The feeding set of claim 1, wherein the plunger of the dispensing control valve includes a plurality of gaskets.

7. A feeding set with an attachment mechanism for use with an enteral feeding pump, the feeding set comprising:
a dispensing control valve having a plunger positioned at least partly therein and at least one clip extending therefrom, the at least one clip configured to engage with a first portion of an internal panel of an enteral feeding pump and the plunger configured to selectively control a flow of fluid through the dispensing control valve;
a peristaltic, first tubing element fluidly connected to an exit of the dispensing control valve, the peristaltic, first tubing element being elastomeric;
a retention disk configured to engage a second portion of the internal panel and the peristaltic, first tubing element pulling the retention disk upward, through tension, toward the dispensing control valve and into engagement with the second portion of the internal panel, such that the feeding set retains its connection with the internal panel of the enteral feeding pump via the at least one clip and the retention disk;
a second tubing element for fluidly connecting at least one bag of fluid to the dispensing control valve; and
a third tubing element configured to be fluidly connected to the peristaltic, first tubing element and the third tubing element having a patient coupling fitted thereto.

8. The feeding set of claim 7 wherein the dispensing control valve has one of feed and flush ports, a feed port, or a flush port.

9. The feeding set of claim 7 wherein the dispensing control valve has a feed port and a flush port and the at least one clip of the dispensing control valve includes a first attachment clip associated with the feed port and a second attachment clip associated with the flush port.

10. The feeding set of claim 7 wherein the at least one clip has a hook configuration that extends from an upper surface of the dispensing control valve.

11. The feeding set of claim 7 wherein the has a plurality of gaskets.

12. The feeding set of claim 11 wherein the plunger further comprises multiple narrow portions that have at least portions with a smaller diameter as compared to plunger portions having a gasket associated therewith, wherein the portions with the smaller diameter permit fluid to move therealong.

13. The feeding set of claim 12 wherein the dispensing control valve includes a feed port and a flush port, and the plurality of gaskets of the plunger includes three gaskets, and the plunger is reciprocal between a feed configuration, a flush configuration, or a no-flow configuration based the position of the three gaskets, wherein the plunger and the three gaskets are moved via a grip that is configured to mate with a knob on a reciprocating arm that is rotatably attached to the internal panel.

14. The feeding set of claim 13 wherein the first portion of the internal panel comprises a first edge and the second portion of the internal panel comprises a second edge and wherein the internal panel further comprises a pie-shaped depression configured to house the reciprocating arm with the knob associated therewith.

15. The feeding set of claim 14 wherein the internal panel further comprises an arcuate depression partially extending from the first edge to the second edge configured to seat at least a portion of the peristaltic, first tubing element and the dispensing control valve therein and the first edge and the second edge are disposed on opposite edges of the internal panel.

16. The feeding set of claim 7 wherein the retention disk comprises a tapered section to connect to the peristaltic, first tubing element, a flange, and a collar.

17. The feeding set of claim 16 wherein the flange comprises an outer ring disposed on a first side facing the tapered section, wherein the outer ring defines a flange depression between the tapered section and the outer ring.

18. The feeding set of claim 17 wherein the internal panel has at least one of an extension or a depression configured to mate with the outer ring or the flange depression to mate the retention disk with the internal panel via the upward force on the retention disk resulting from the elastomeric material of the peristaltic, first tubing element.

19. The feeding set of claim 17 wherein the outer ring has an angled surface that facilitates engagement of a first side of the flange of the retention disk with a lower edge of the internal panel.

20. The feeding set of claim 17 wherein the third tubing element is fluidly connected to the peristaltic, first tubing element via the retention disk, where the tapered section of the retention disk extends into the peristaltic, first tubing element and an end of the third tubing element is disposed within the collar of the retention disk.

21. The feeding set of claim 7 further comprising at least one spike cap configured to protect at least one end of the second tubing element.

22. The feeding set of claim 7 wherein the enteral feeding pump further comprises a pump door hingedly attached to a housing body, wherein the pump door moves from a first position to a second position, wherein the first position closes the pump door and further secures the internal panel, the peristaltic, first tubing element, and the dispensing control valve of the feeding set relative to a remainder of the enteral feeding pump and the internal panel has a rectangular opening therein through which a plurality of keys extend that are configured to advance in a sequential manner to move the fluid through the peristaltic, first tubing element.

23. The feeding set of claim 22 wherein the feeding set remains securely attached to the enteral feeding pump when the pump door is in an open position via the at least one clip and the retention disk.

24. A method of providing an enteral feeding pump for use with a nutritional liquid and a feeding set, the method comprising:
   attaching a first portion of the feeding set to a panel of the enteral feeding pump via at least one first retainer of a dispensing control valve that is attached to a first edge of the panel;
   attaching a second portion of the feeding set to the panel via a second retainer that is associated with a second edge of the panel; and
   moving a plunger at least partly disposed in the dispensing control valve to adjust a flow of fluid therethrough.

25. The method of claim 24 wherein the plunger disposed is laterally moved to open one of a feed line or a flush line.

\* \* \* \* \*